United States Patent [19]

Fukuoka

[11] 4,033,054

[45] July 5, 1977

[54] FOOTWEAR

[76] Inventor: Tatsuo Fukuoka, No. 3-3, 2-chome, Shinminamifukushima, Tokushima, Japan

[22] Filed: Aug. 11, 1976

[21] Appl. No.: 713,596

[30] Foreign Application Priority Data

Aug. 11, 1975 Japan .................. 50-111838[U]

[52] U.S. Cl. .................. 36/11.5; 36/91; 128/582
[51] Int. Cl.[2] .................. A43B 3/12; A43B 7/22; A61F 5/14
[58] Field of Search .................. 36/11.5, 88, 91, 43, 36/44, 32 R, 25 R; 128/582, 64

[56] References Cited

UNITED STATES PATENTS

| 1,867,679 | 7/1932 | Reihle et al. | 36/91 |
| 3,595,244 | 7/1971 | Kugler | 36/11.5 |
| 3,992,788 | 11/1976 | Orien et al. | 36/91 |

*Primary Examiner*—Patrick D. Lawson
*Attorney, Agent, or Firm*—Wenderoth, Lind and Ponack

[57] ABSTRACT

A footwear is provided with pressure projections adapted to pressure-stimulate effective spots of a foot and provide simulated finger-pressure treatment. Each of the pressure projections has a magnet for applying magnetism to the effective spots. The effective spots of the foot are therefore subjected to the multiple stimulating effects obtained by the pressure stimulation due to the pressure projections and the magnetic stimulation due to the magnets.

16 Claims, 38 Drawing Figures

FOOTWEAR

The present invention relates to a type of footwear which can stimulate effective portions of a foot by simply wearing the same to change the condition of the distal circulation system and supply the foot with more blood, thereby achieving a condition in which the head is cool and the feet warm. In this manner, not only various kinds of chronic diseases can be effectively cured, but improvement of health and prevention of disease can be achieved.

BACKGROUND OF THE INVENTION

A number of effective spots for finger-pressure treatment are distributed over a foot. Such effective spots are medically considered as where the sympathetic nerve distributed in the skin is excited. Therefore excitation of the sympathetic nerve provides effective spots. Further, the sympathetic nerve and the para-sympathetic nerve in combination are called the autonomic nerve. When the sympathetic nerve is controlled, the para-sympathetic nerve is also controlled. Therefore, by controlling the sympathetic nerve, the antonomic nerve is controlled. The antonomic nerve is one which controls involuntary functions, such as the internal organs, i.e., the stomach, intestines, heart, womb, bladder, endocrine glands, sweat glands, salivary glands, pancreas and the like, and effectively sustains the life in a body. The autonomic nerve can be adjusted to maintain a normal state by pressure and magnetic stimulation of the effective spots of the related sympathetic nerves. Therefore, by stimulating the effective spots, various kinds of diseases, especially chronic illnesses incurable with medicines or the like can be radically and perfectly cured without harmful side effects. An example of this is gastric hyperacidity. Sodium bicarbonate is applied for neutralizing acid in the stomach, but carbonic acid gas generated during the neutralization of acid in the stomach with sodium bicarbonate stimulates the gastric wall to secrete more gastric juice and result in the failure to radically cure the illness. Further, in case of bronchial asthma, medicines, e.g., ephedrin, for dilating the trachea are generally administered, but they are effective only during the administration and are incapable of curing asthma per se. Such treatments only temporarily restore the normal function of the affected area, and satisfactory effects cannot be expected for chronic illnesses.

Furthermore, magnetism of a magnet not only magnetically stimulates the effective spots to control the autonomic nerves but has an excellent influence upon the circulation of blood. That is, in accordance with Fleming's law, electrons are generated in the blood flowing at right angles to the magnetic force, depending upon the flow and the rate of the blood, and the electrons purify the blood per se and promote the blood circulation. Magnetism also acts on hemoglobin, oxygen and carbon in the blood and body fluids to improve and strengthen their activity. Therefore, various kinds of illnesses, especially quasi-health symptoms can be effectively cured by the application of magnetism. Particularly, stimulation of the effective spots on a foot improves the blood circulation, supplies the foot with blood and makes the foot warmer. This brings an ideal healthful condition, the so-called "cool head and warm foot" condition, thus effectively curing various kinds of quasi-health symptoms.

The effective application of magnetism from a magnet and the promotion of the effectiveness thereof depend upon the manner and degree of close contact of the magnet with the sole of the foot. This is because the effectiveness of the magnetism exerted on the foot is determined by the intensity of the magnetic field on the foot produced by the magnet. The intensity of a magnetic field is reduced in proportion to the distance of the foot from the magnetic. Consequently, when the magnet is remote from the sole of the foot, the intensity of the magnetic field is remarkably reduced, resulting in failure of any effective application of the magnetic force. However, by attaching a magnet directly to the portion of a sole of a footwear with which a foot is always in close contact, the magnet is always in close contact with the foot. In most cases, however, magnets are generally secured to the footwear at positions of the effective spots which do not contact with the foot, e.g., near the arc of the foot sole or the bases of five toes. Therefore, by only securing magnets onto the sole of a footwear, the magnets do not closely contact the foot, and a space therebetween is established, thereby remarkably reducing the intensity of the remarkably reducing the intensity of the magnetic field of the foot.

According to the present invention, pressing projections adapted to stimulate, by pressing, the effective spots of a foot are provided on the inside of a footwear, and said projections are further provided with a magnet, whereby the effective spots of the foot are magnetically stimulated as well as being subjected to said pressure stimulation. In the case of pressure projections without magnets, such projections are attached to the sole or insole; then, when the sole is firmly under the foot, strong pressure stimulation is achieved. Otherwise, the projections cannot strongly press the effective spots. Such pressure projection can press the effective spots only temporarily and cannot press continuously. By providing high pressure projections, the skin of a foot is pressed thereby with strong pressure. However, if the projections firmly under the foot are too high they press the skin of the foot with excessive pressure, and hurt the foot, thereby remarkably lowering the comfort of the footwear.

BRIEF SUMMARY OF THE INVENTION

An important object of the present invention is to provide a footwear by which the effective spots of a foot are subjected to multiple stimulation of pressure projections and magnets in combination to adjust the autonomic nerves, whereby various kinds of illnesses, especially quasi-health symptoms and various kinds of chronic illness can be radically cured.

Another important object of the present invention is to provide a footwear which stimulates the effective spots of the foot by pressure projections and at the same time magnetically stimulates the foot with magnets, so that a multiple stimulating effect is achieved, thereby obtaining a more excellent stimulating effect.

Another important object of the present invention is to provide a footwear which continuously stimulates the effective spots of a foot by only wearing the footwear. If necessary, such stimulation can be stopped immediately by removing the footwear.

Another important object of the present invention is to provide a footwear which promotes health, increases bodily strength, and which can be obtained by an inexpensive footwear suitable for popular daily use, e.g., a sandal or a shoe.

Accordingly, the present invention comprises a footwear in which each pressure projection is provided with a magnet so that the effective spots for finger-pressure treatment of a foot are magnetically stimulated continuously even if the foot comes more or less apart from the footwear.

BRIEF DESCRIPTION OF THE DRAWINGS

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

The invention will be understood more readily by reference to the following examples; however, these examples are intended to illustrate the invention and are not to be construed to limit the scope of the invention.

DETAILED DESCRIPTION OF THE INVENTION

Figure 1:
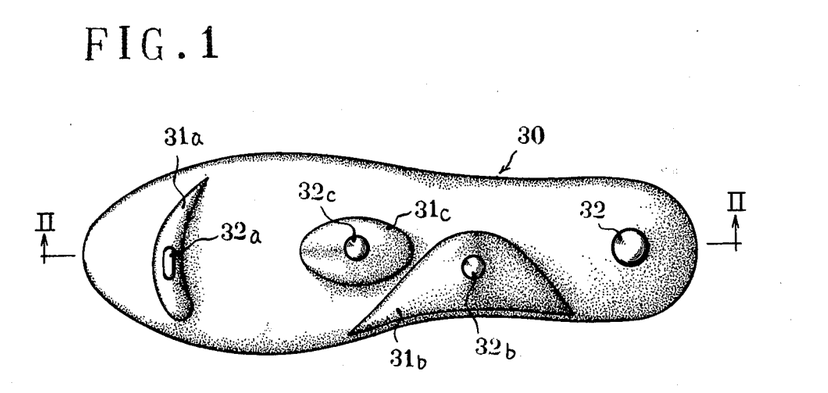
FIG. 1 is a plan view of an embodiment of a sole according to the present invention.
Figure 2:
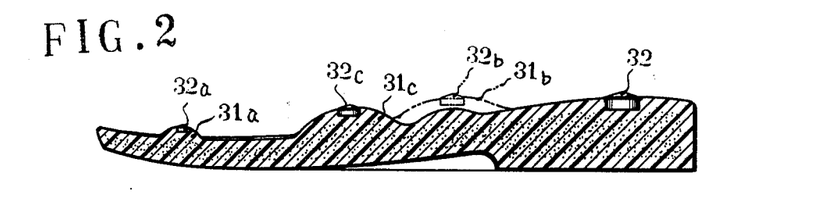
FIG. 2 is a sectional view taken along the line 2—2 in FIG. 1.

A sole 30 shown in FIGS. 1 and 2 is provided with a crescent-shaped pressure projection 31a near the base of the toes, a semicircular pressure projection 31b on the arched portion, and an elliptical pressure projection 31c at a point corresponding to "Yusenbu" (it means "spring portion" in Japanese and indicates a specified effective spot for finger-pressure treatement) little forward from the arched portion toward the center of a foot. The pressure projections 31a, 31b and 31c are each provided on the top portion thereof with magnets 32a, 32b, 32c, respectively.

Figure 3:
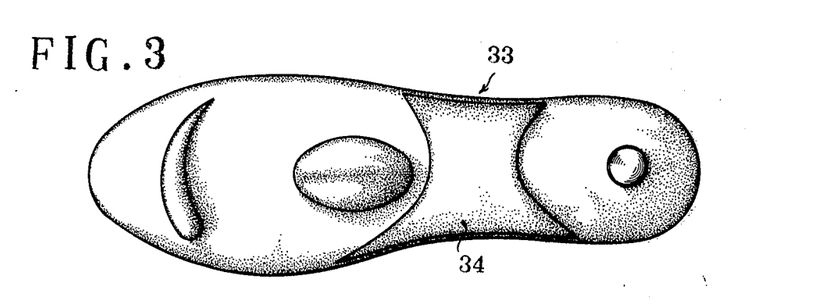
FIG. 3 is a plan view of another embodiment of a sole according to the present invention.

In a sole 33 shown in FIG. 3, a pressure projection 34 on the arched portion is formed into an elongated shape across the sole. This pressure projection 34 is adapted to press the central portion including the arched portion of a foot and has the same pressure effect as obtained by treading on a half of a split bamboo (a green bamboo).

A presure projection may be formed into, for example, an angled shape so that the recessed portions, e.g., the arched portion of a foot can be effectively pressed. Particularly, pressure projections adapted to press the foot portion near the base of toes are formed in an elongated angled shape in horizontal section with the protruding bottom portion.

The sole 30 and the pressure projections are integrally molded from a synthetic resin, and a magnet 33 is fitted near the top of each projection.

Figure 4:
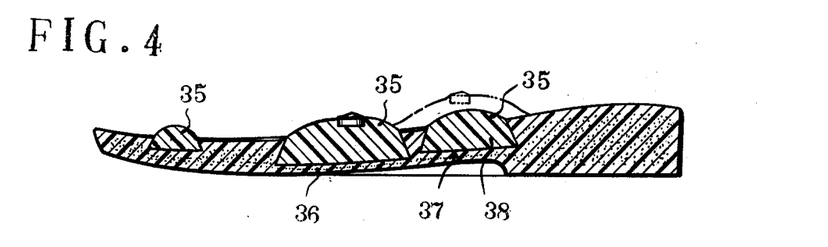
FIG. 4 is a longitudinal sectional view of another embodiment of a sole according to the present invention.

The present invention, however, is not limited to a construction in which the sole and pressure projections are integrally molded. For example, as shown in FIG. 4, a pressure projection 35 may be formed separately from a sole 36 and then fitted to the latter, thereby permitting pressure projections to be fitted onto a conventional flatsurfaced sole. In this case, pressure projections formed separately from a sole may be fitted onto the sole using an adhesive or another suitable means. Further, by adhering pressure projections to the upper surface of a sole by means of a two-sided adhesive tape, a magic band or the like, the positions of the pressure projections are easily and correctly adjusted so as to correspond to the effective spots of the individual wearer's foot according to the size of his foot and his demand.

Figure 5:
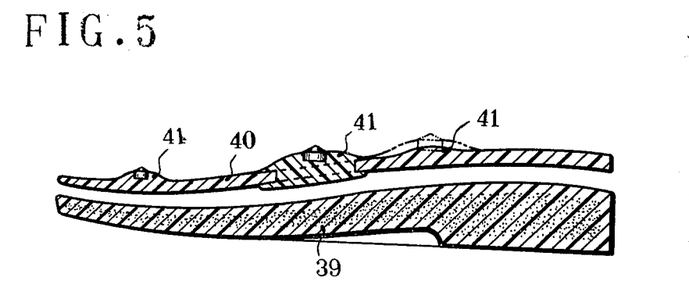
FIGS. 5 and 6 are longitudinal sectional views of other embodiments of a sole according to the present invention.

When pressure projections are provided so as to press the sole, they are generally fitted onto the sole surface of the footwear, but as shown in FIG. 5, a sheet member 40, such as an inside sheet or an insole, may be provided with pressure projections 41. A sheet member of such a structure can be easily inserted in a conventional footwear, and since it is not necessary to provide the sheet member 40 with a strength similar to that of a sole, the member 40 may be formed from a soft and elastic material, thereby permitting a magnet on the projection to more closely contact the foot.

Figure 6:
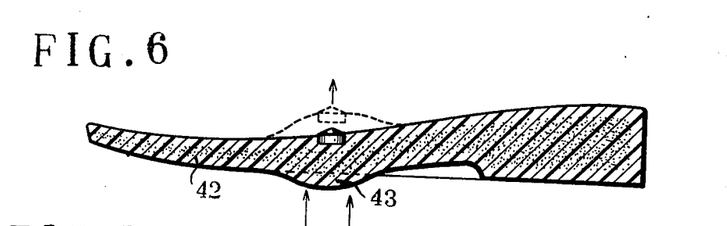

A sole 42 shown in FIG. 6 is provided on its lower surface with a pressure projection 43 and has such a flexibility that at least the portion near the projection 43 of the sole and in most cases the whole of the sole can be deformed to protrude upwardly as shown with a dash-and-dot line in the figure, when firmly under a foot. When the sole 42 and the pressure projection 43 are integrally molded as shown in FIG. 6, the sole 42 is required to be soft and elastic. A flexible sole provided on its lower surface with a pressure projection being flexible at least near the projection so as to permit the projection to protrude upwardly when firmly underfoot is highly effective, because the projection does not interfere with putting the footwear on, and with a large-sized pressure projection, a high pressure effect can be obtained. Further, the largest pressure projection does not influence the size of a band across the upper portion of the foot due to its situation on the lower surface. That is, if a pressure projection of any shape and size is provided at any position on the lower surface of a sole, the sole and its band always fit a foot well, and the pressure projection raised when trodden by the foot properly stimulates the foot.

The pressure projections are generally formed from soft and elastic material. A magnet provided on the projection always comes into contact with the sole of the foot due to the elastic deformation of the projection. Therefore, the effective spots for pressure treatment are effectively, magnetically stimulated by a more intense magnetic field.

The effective spots of the foot are not only distributed on the sole of the foot. Therefore, the pressure projections are not always provided on the sole, but may be on the upper portion of a shoe or on a band of a sandal.

Figure 7:
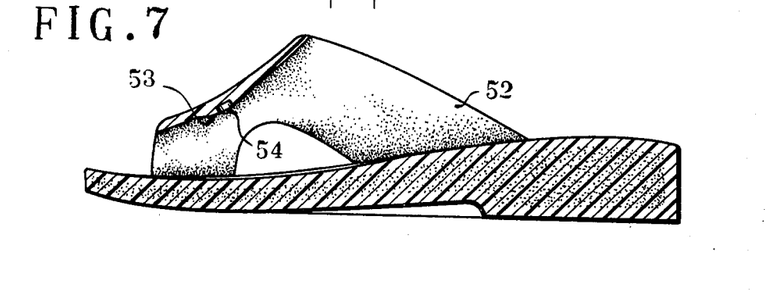
FIG. 7 is a longitudinal sectional view of an embodiment of a sandal according to the present invention.

FIG. 7 illustrates a sandal in which a pressure projection 53 is provided on a band 52, said projection 53 including a magnet 54.

When the magnet 32 protrudes above the projection 31 as shown in FIG. 2, the effective spots on the surface of the skin of a foot can be stimulated directly by the magnet 32.

Figure 8:
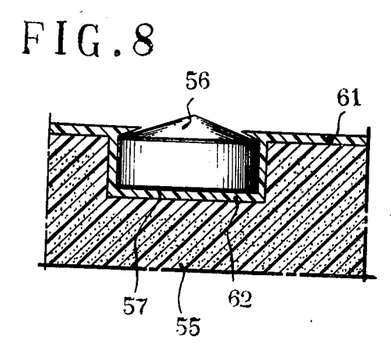
FIGS. 8 and 9 are sectional views illustrating the fitting of a magnet.
Figure 9:
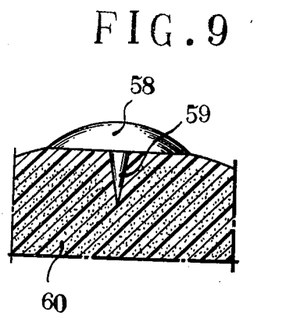

If the pressure projection is formed from a rather soft material, the magnet can be secured to the projection most easily by providing a hole 57 in the projection 55 for fitting the magnet 56 as shown in FIG. 8 and then inserting the magnet 56 into the hole 57. Alternatively, as shown in FIG. 9, the fitting may be achieved by providing a pin 59 on the lower surface of a magnet 58, and then pushing the pin 59 into the pressure projection 60.

Figure 10:
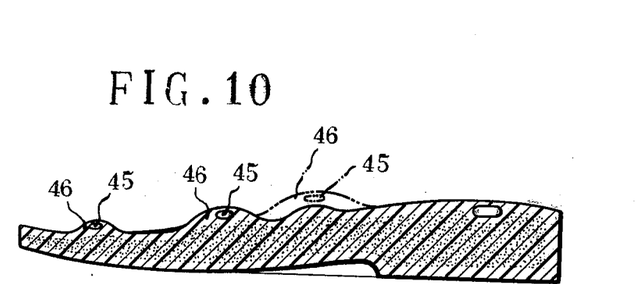
FIG. 10 is a longitudinal sectional view of another embodiment of a sole according to the present invention.

Further, as shown in FIG. 10, when the pressure projection 56 is molded from a synthetic resin, the magnet 45 may be inserted so as to be wholly embedded in the projection 40.

On the other hand, when a magnet is fitted on the upper portion of the pressure projection and is adapted to contact the sole of the foot, the magnet is always pushed into a fitting hole in the projection by the foot and is prevented from being detached.

Figure 11:
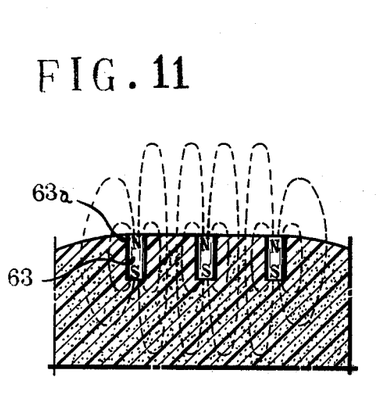
FIGS. 11 and 12 are sectional views of pressure projections each provided with a plurality of magnets.
Figure 12:
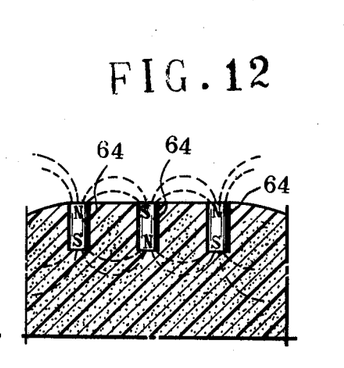
Figure 13:
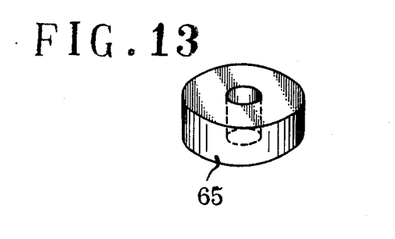
FIGS. 13 to 16 are perspective and plan views of magnets to be used according to the present invention.
Figure 14:
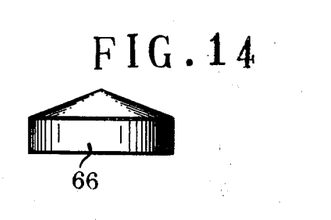
Figure 15:
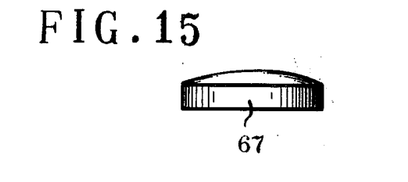
Figure 16:
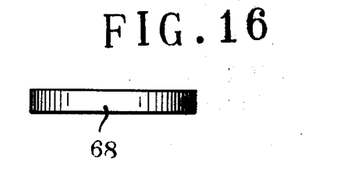

The distribution of magnetic fields can be adjusted by providing a plurality of magnets adjacent to one another. As shown in FIG. 11, one pole 63a of a magnet 63 is directed toward the skin of the sole of the foot, and all of the other eternal magnets 63 are arranged in the same direction, e.g., with the N pole on the upper side. The magnetic force lines generated from each of the poles repel one another and are directed in parallel with the direction of the pole, whereby strong magnetic force reaches a position at a distance from the poles. The intensity of a magnetic field at a point in this arrangement is equal to the vector sum of the intensities of the magnetic fields produced by the magnets respectively. But, if a plurality of magnetic fields exist adjacent to one another, all of the magnetic fields produced by the poles respectively are directed substantially in the same direction as they are farther from the poles, and therefore, the intensity of the magnetic field at a certain point becomes higher because it comprises the algebraical sum of the intensities of the magnetic fields produced by the poles respectively. As the result, the magnetic field at a point far from the poles becomes intense and magnetism can be applied not only to the skin but the inner portion of a foot. However, as shown in FIG. 12, when magnets 64 are arranged so that two adjacent magnets have poles opposite to each other, i.e., with the upper pole of each of two side magnets being an N pole and that of the central magnet being an S pole as shown in FIG. 12, the intensity of the magnetic field at a point far from the poles is less, and the magnetic force becomes much lower in proportion to the distance from the poles. From this fact, it is said that as the effective spots of a foot come near and far from the magnets, the intensity of the magnetic field varies (but never becomes zero as is the case of a pressure projection without and magnet). Therefore, a stimulating effect is obtained by the change of the magnetic force due to the fluctuating magnetic field. By raising the upper end of the magnet, but not to such an extent as to pain a foot when walking, the magnetic flux can be converged and thereby local treatment of the effective spots is achieved.

As shown in FIGS. 13 to 18, when at least the pole end side of the magnets 66, 67, 68 is formed to have a smooth surface, the pole surface adapted to face the sole of the foot is provided with a uniform magnetic field. Therefore, if the effective spots are displaced more or less from the center of the magnet, but retained within the plane of the magnetic pole, they are subject to an effective magnetic treatment in the constant intensity of the magnetic field. It has been proven by clinical experiments that the diameter of an effective spot of a foot is 2-3 mm$\phi$. Consequently, if a magnet is secured correctly in correspondence with such an effective spot, the diameter of the magnetic pole plane may be 2-3 mm$\phi$. However, the diameter of the magnetic pole plane is selected to be larger than that of an effective spot so that a magnet can apply a constant intensity magnetic field to an effective spot even after its displacement from the center of the magnet, i.e., apply the same equally to every person's effective spot. Simply stated, the area of the magnetic pole plane is preferably larger than 2-3 mm$\phi$. It is a little different and varies according to the fitting position, but the magnetic plane is formed to have a diameter of 1-1.5 cm$\phi$. With a large magnetic pole plane, the position of the magnet need not be strict, and the positioning in fitting operation becomes simple.

Figure 17:
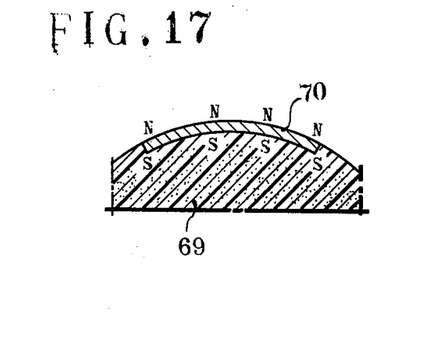
FIGS. 17 and 18 are sectional views of pressure projection provided with a magnet.
Figure 18:
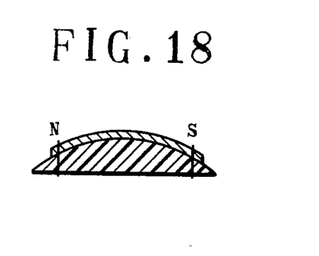

A pressure projection 69 shown in FIG. 17 is provided on its upper surface with a flexible sheet permanent magnet 70 adhered thereto. The upper surface of the magnet 70 is magnetized to be an N pole and the lower surface an S pole. By magnetizing a permanent magnet so that the upper and lower surfaces thereof have opposite poles respectively, the magnetic field produced on the upper surface can be formed uniformly, and an effective spot of the foot on any position of the upper surface of the magnet can be similarly subjected to the magnetic field. Further, as shown in FIG. 18, magnetization may be achieved so that two sides of a magnet have opposite poles, respectively. The sheet magnet is preferably flexible. Such a flexible magnet can be obtained by molding ESD magnetic powder using a non-rigid binding agent, e.g., a non-rigid synthetic resin, rubber or the like. A flexible permanent magnet is effectively prevented from being detached from a pressure projection. Further, a non-rigid sheet magnet can be attached to a pressure projection by seaming or with an adhesive agent.

Such a magnet may be a magnet formed from an alloy, e.g., a ferrite magnet, alnico, samalium cobalt magnet, or a powder magnet, e.g., iron and cobalt magnet or any other magnets. However, a ferrite magnet is most preferably with respect to holding. For decorating the surface of a magnet, the magnet may be plated, coated with ceramic, or embedded wholly into a pressure projection.

A non-rigid magnet is preferable because it is capable of integral formation with a pressure projection. That is, a pressure projection is formed from a non-rigid magnet. The integral formation of a magnet and a pressure projection saves the fitting operation of the magnet to the projection as well as prevents the detachment of the magnet from the projection.

Figure 19:
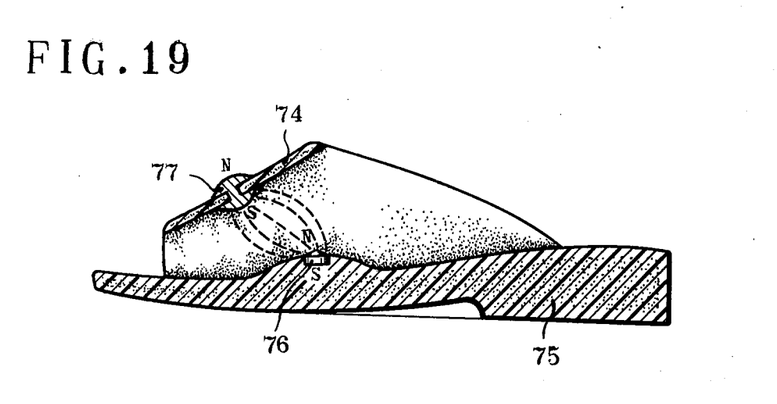
FIG. 19 is a longitudinal sectional view of another embodiment of a sandal according to the present invention.

Further, referring to FIG. 19, two magnets 76, 77 are provided in an opposing manner on the upper portion of an upper band and/or a sole respectively. With this arrangement of two magnets 76, 77, the magnetic flux can penetrate into the inner portion of the foot or apply only to the surface of the foot. This is because, when two opposite magnetic poles are in face-to-face arrangement as shown in FIG. 19, a magnetic flux from one pole is extracted toward the other, and thus penetrates the foot. When the same polarities are in face-to-face arrangement, the fluxes from the two poles repel each other, and at the middle portion, the magnetic field becomes zero, whereby more flux is applied onto the surface of the foot. Thus, by changing the polar intensity, shape and fitting position of the magnets to be attached to the upper band and the sole, a foot can be selectively subject to three-dimensional and local magnetic application.

Figure 20:
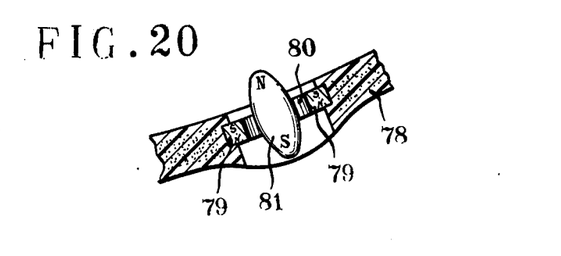
FIG. 20 is a sectional view of a band fitted with a magnet.

FIG. 20 illustrates another embodiment in which a magnet is attached to a band 78 of a sandal. A ring-shaped stationary magnet 79 is secured to the band 78, i.e., a sheet member, and a movable magnet 81 is movably inserted into a through hole provided in the stationary magnet 79. The movable magnet 81 is retained in the hole 80 by the magnetic attractive force of the two magnets. The stationary magnet 79 is formed into a circular or polygonal ring of required thickness and its two surfaces are magnetized to be of opposite polarities. The through hole 80 is of such a dimension that the movable magnet 81 having a required size can move freely in the axial direction (vertically to FIG. 20). This movable magnet 81 capable of moving freely in the axial direction as above-mentioned may be formed in any shape as long as it is permitted to generate a predetermined magnetic power line. However, by forming the magnet 81 to be elliptical or circular in vertical section, and by selecting its length larger than the thicknesss of the stationary magnet and the sheet member so as to protrude slightly above and below the stationary magnet and the sheet member, the movable magnet presses the surface of the skin of a foot with suitable pressure, thereby providing a pressing effect as well as that of magnetism application.

The movable magnet is to be held within the through hole in the stationary magnet by the magnetic attractive force produced between the stationary and movable magnets. Thus, the movable magnet is magnetized so that each of its two surfaces has a polarity opposite to that of the corresponding surface of the stationary surface as shown in FIG. 20, thereby the movable magnet is attracted toward the center of the through hole. That is, when the upper surface of the stationary magnet 79 is an N pole, that of the movable magnet 81 is magnetized as an S pole.

The effect of the magnetic treatment depends upon the intensity of the magnetic field applied to the part to be treated. The intensity of the magnetic powder of the magnetic field is in proportion to the magnetic power of the magnet, and in inverse proportion to the self-multiplication of the distance from the magnet. Consequently, the improvement of the effect of the magnetic treatment by the intensity of the magnetic field depends upon the possibility of closely contacting the magnet with the effective spot of the foot sole. By providing the magnet on or near the top of the pressure projection, the magnet comes near the effective spot on the sole of the foot and shortens the distance between the magnet and the sole. Thus the intensity of the magnetic field applied to the effective spot is increased, and the effective spot is effectively stimulated by a magnetic field of high magnetic flux density.

The intensity of magnetic force, however, never becomes zero even at a distance from the magnet. Therefore, by positioning a magnet between effective spots a plurality of effective spots can be magnetically stimulated indirectly by one magnet.

According to a footwear in which a magnet is mounted on or near the top of each of the pressure projections so that the effective spots of the foot are subject to pressure stimulation by the pressure projections and magnetic stimulation by the magnets in combination, the effective spots can be further subjected to the multiplied stimulating effect of continuous stimulation by the magnet and the intermittent pressure stimulation by the projection. Thus, a remarkably high treating effect has been realized. Such a multiplied stimulation by the pressure projection and the magnet is more effective than the constant intensity of continuous stimulation as well as intermittent stimulation, because the same effective spot is subjected to both pressure and magnetic stimulations. At the same time, said two kinds of stimulations continue but always change their condition. Further, since a footwear is an inexpensive product of popularly daily use, the promotion of health and improvement of the bodily strength can be realized on a nationwide scale by providing footwear with pressure projections and magnets. Further, since most footwear is manufactured so as to fit each person, pressure projections and magnets can be provided so as to correctly correspond to the positions of the effective spots of each person's foot, thereby achieving a high treating effect for every person.

The advantageousness of the footwear according to the present invention was tested in many practical respects, and more effective results than expected were obtained as shown in the following description given with reference to the drawings.

According to the results of the sampling of 39 persons having subjective sympton, the most apparent improvement achieved by wearing a sandal according to the present invention was the temperature raise in their feet. Consequently, the change of the condition of the distal circulation system, especially the temperature change in feet was observed. The test was carried out on 14 men and 2 women from 22 to 44 years old. The instruments used were a Thermohear MB by Nippon Denshi Co., Ltd. and a Thermister by Nippon Koden Co. Ltd. for measuring the skin temperature of the foot. In order to dynamically catch the change of the condition of the distal circulation system in foot, the persons were tested during the 30 minutes immediately following standing up from a lying position. Measurement was carried out once with a conventional sandal with a flat upper sole surface and two times, i.e., the third and fifth days, the sandal according to the present invention shown in FIG. 1 and 2 (hereinafter referred to as the inventive sandal). The test was per-formed at a constant temperature of 25° C with 60% of moisture.

Figure 21:
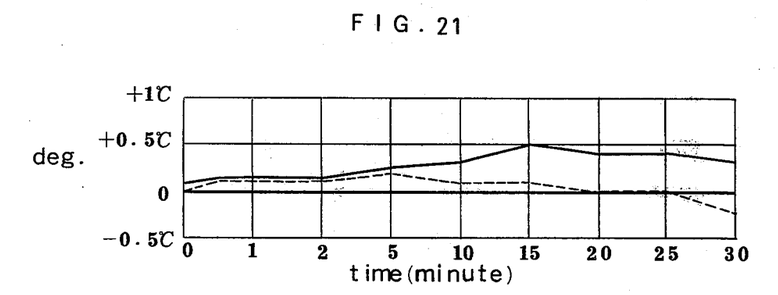
FIGS. 21 to 29 are graphs illustrating the body temperature changes of persons when wearing a conventional sandal and a sandal according to the present invention.
Figure 22:
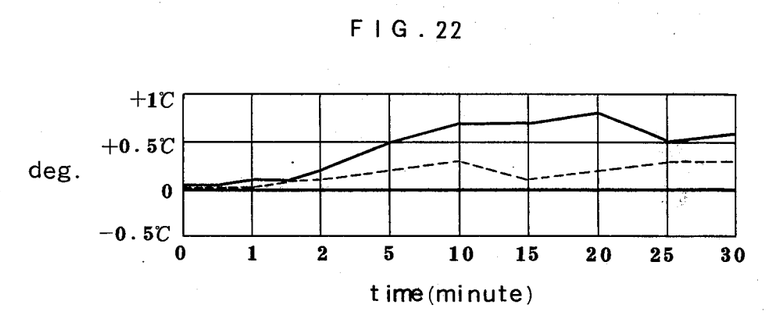
Figure 23:
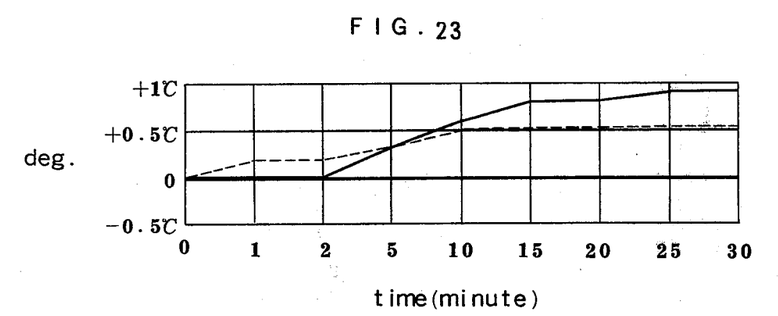

In FIGS. 21 to 23, the temperature of the toes of persons wearing the inventive sandal is shown in a broken line, and the temperature of the inner portion of the foot is shown by the solid line.

FIG. 21 shows the temperatures of feet wearing a conventional sandal, and FIGS. 22 and 23 show such temperatures on the 3rd and 5th days of wearing the inventive sandal. The temperature in each of the drawings are the mean values obtained from 11 persons.

As seen from FIGS. 21 to 23, the wearers of the inventive sandal show an increase to both the temperatures of the skin and the inner portion. With the conventional sandal, the temperature of the inner portion raised 0.5° C at most after 15 minutes, while with the inventive sandal, the temperature rise was 0.8° after 20 minutes on the third day and 0.9° C after 25 to 30 minutes on the fifth day. Further, with regard to the temperature of the skin, when wearing the conventional sandal the rise was 0.15° C, while wearing the inventive sandal raised the temperature 0.3° on the third day and 0.5° C on the fifth day.

Figure 24:
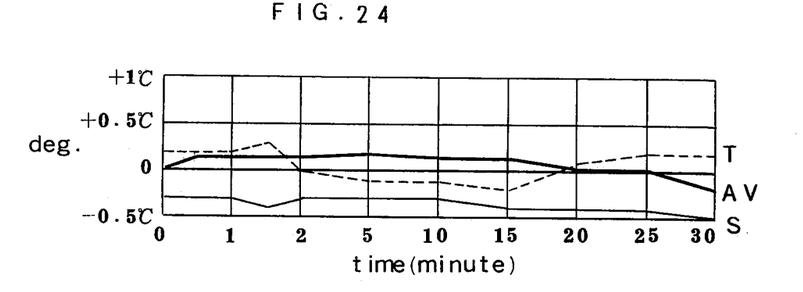
Figure 25:
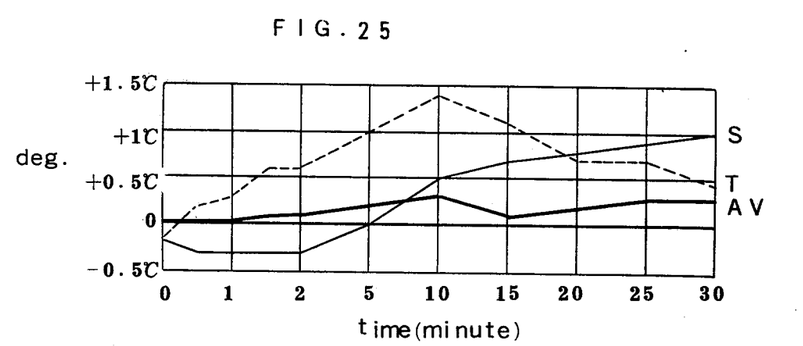
Figure 26:
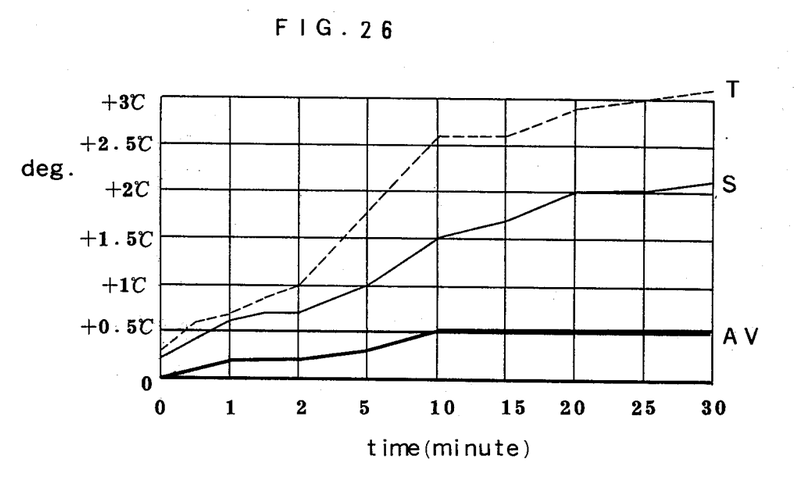

FIGS. 24, 25 and 26 show the temperature changes of the skin of the toes when a conventional sandal was worn, and the inventive sandal on the third day of wearing, and the inventive sandal on the fifth day, respectively. The full line AV, the dotted line T and the thin line S indicate the mean value relating to eleven persons, the temperature change of a 24 year old man and that of a 44 year old woman, respectively. The mean temperature rise relating to the eleven persons was 0.15° C after 5 minutes when wearing the conventional sandal, while it was 0.3° C on the third day and 0.5° C on the fifth day. The temperature of the skin of the 44 year old woman dropped when wearing the conventional sandal, but by wearing the inventive sandal, it began to rise after only in 2 minutes and on the third day it increased 1° C in 30 minutes, and on the fifth day it never showed any drop but increased 2.1° C. The 24 year old man wearing the inventive sandal experienced a maximum temperature rise of 1.4° C on the third day and a remarkable rise of 3.1° C on the fifth day.

Figure 27:
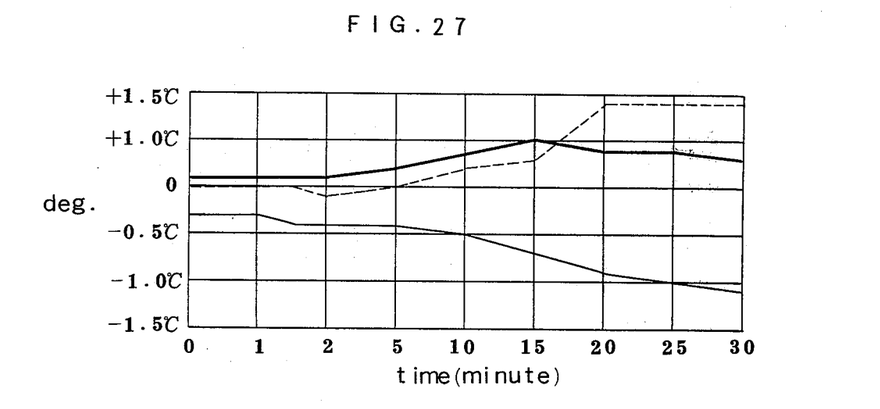
Figure 28:
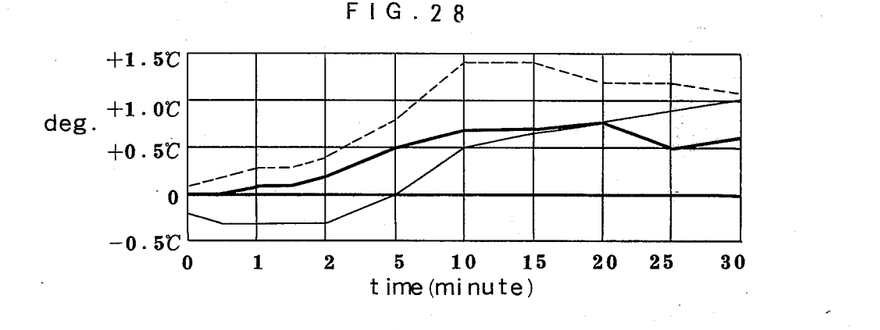
Figure 29:
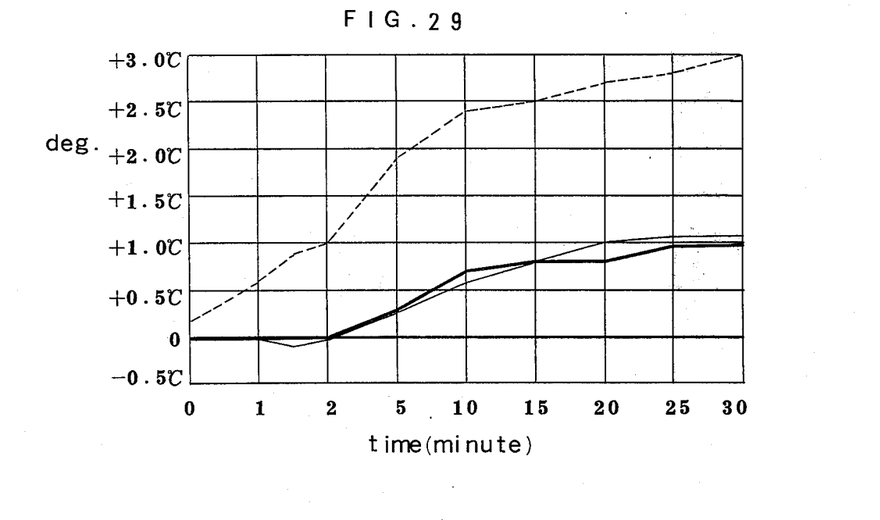

FIGS. 27, 28 and 29 show the temperature changes of the inner portion of the foot when wearing the conventional sandal, the inventive sandal on the third day of wearing and the inventive sandal on the fifth day, respectively. The full line AV, the dotted line T, and the thin line S indicate the mean value relating to 11 persons, the temperature change of a 24 year old man, and that of a 44 year old woman, respectively. As shown in FIG. 27, the mean value of the temperature rise relating to the eleven persons was 0.5% C when wearing the conventional sandal, but it was 0.8° C on the third day and 0.9° C on the fifth day when wearing the inventive sandal, as shown in FIGS. 28 and 29. The temperature rise of the 24 year old man was 0.8° C while wearing the conventional sandal, but it was 1.4° C on the third day and 3° C on the fifth day while wearing the inventive sandal. Further, the temperature of the 44 year old woman showed more than 1° C drop by wearing the conventional sandal, and to the contrary, it showed 1° C rise on both the third and fifth days when wearing the inventive sandal.

Figure 30:
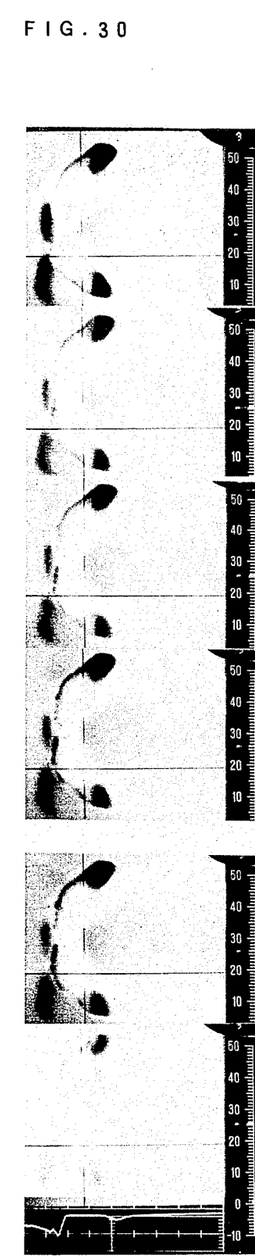
FIGS. 30 to 37 are photographs of thermographs illustrating the foot temperature change of a person when wearing a conventional sandal and a sandal according to the present invention.
Figure 31:
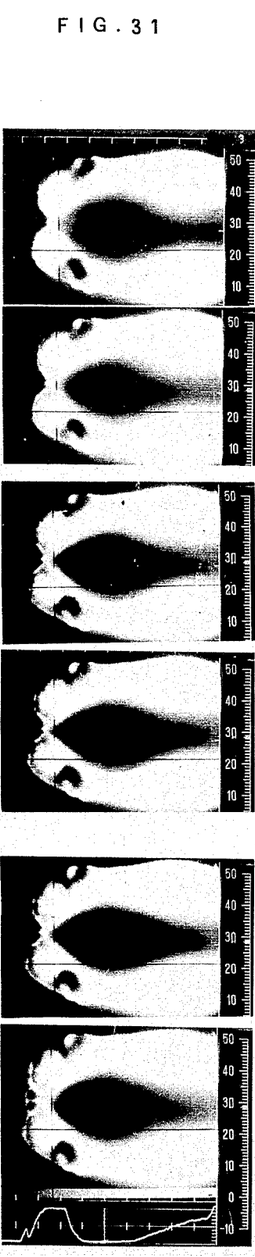
Figure 32:
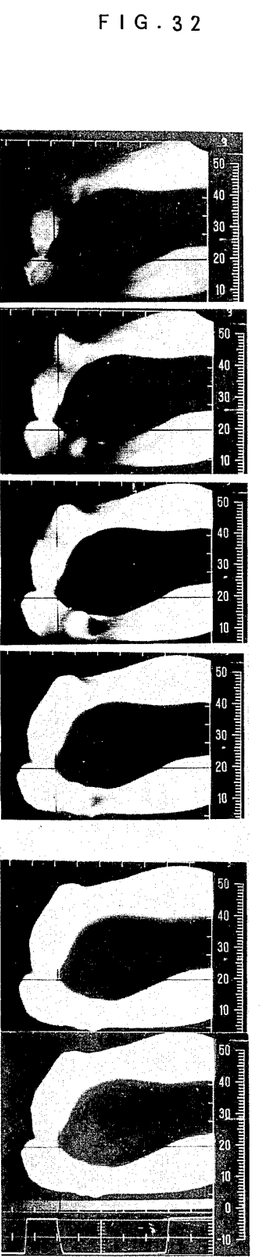
Figure 33:
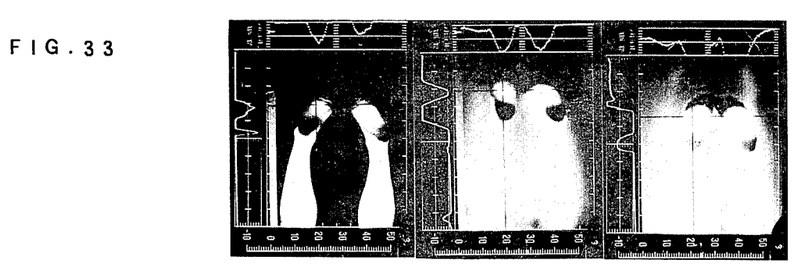
Figure 34:
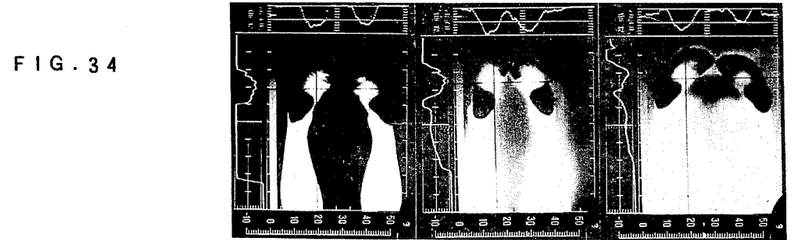
Figure 35:
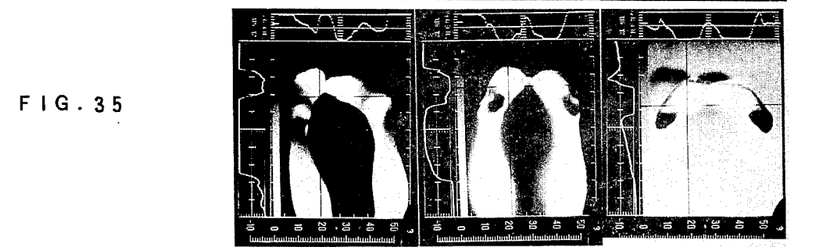
Figure 36:
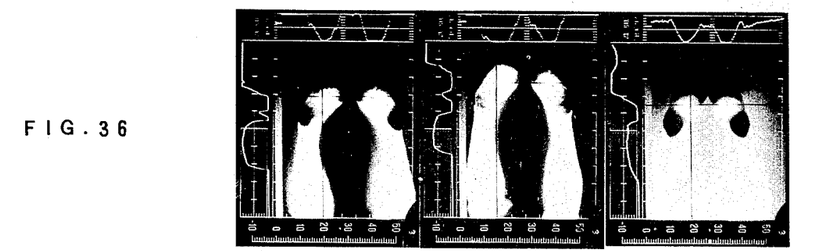
Figure 37:
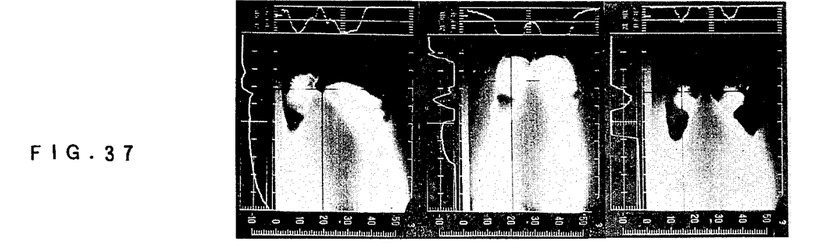

FIGS. 30, 31 and 32 show the temperature of the skin of the foot measured by thermography when the conventional sandal is worn, on the third day of wearing the inventive sandal, on the fifth day of wearing the inventive sandal, respectively. In each figure, there are shown the temperatures immediately after standing up from the lying position, and after 3, 5, 7, 10 and 15 minutes in this order from the upper one downward. As is apparent from these figures, the sole of a person wearing the conventional sandal is black, i.e., has a low temperature, while that of a person wearing the inventive sandal is white, i.e., has a higher temperature.

FIGS. 33 to 37 also show the thermographies. In each figure, there are shown the temperatures of the feet of persons wearing the conventional sandal, those wearing the inventive sandal on the third day, and those wearing the inventive sandal on the fifth day, in this order from the left to right.

Figure 38:
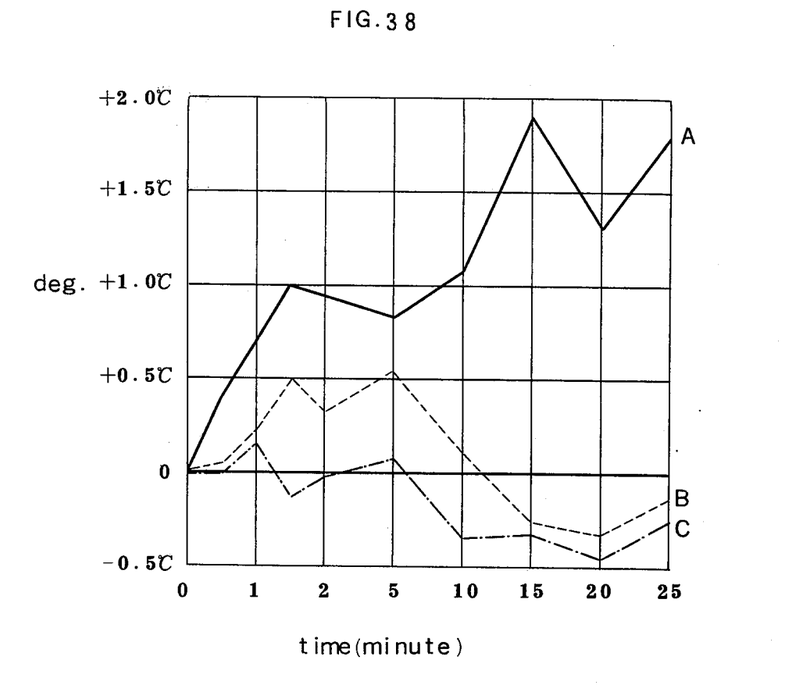
FIG. 38 is a graph illustrating the hand temperature change.

FIG. 38 shows graphically the change of the condition of the distal circulation system of the upper limb, i.e., the temperature change a finger, in which the curvatures A, B and C illustrates the temperature change of the fingers of persons wearing the conventional sandal, those wearing the inventive sandal on the third day and those wearing the inventive sandal on the fifth day, respectively. When the conventional sandal was worn, the temperature of the finger began to rise immediately after putting it on, but when the inventive sandal was worn, the temperature dropped. The graph shows the drop of the temperature of the finger, and the former graph and the thermography show the rise of the temperature of the foot. This means that more blood is supplied from the hand toward the foot to raise the temperature of the foot, whereby the distal circulation system is changed into an ideal condition of the so-called "cool head with warm feet".

As is apparent from the drawings, the mean value of the temperature rise of persons wearing the inventive sandal is 1.5° – 2.5° C.

From these results, it has been shown numerically that wearing the inventive sandal causes the temperature of the foot to rise. Further, the results of the survey of the wearers has shown that while wearing the inventive sandal the feet become warm, the shoulders become relaxed, sound sleep becomes possible, and the like.

What is claimed is:

1. A footwear provided with at least one pressure projection adapted to pressure stimulate effective spots of a foot for pressure treatment, said pressure projection being provided on or near its top portion with a magnet.

2. A footwear as claimed in claim 1, in which said pressure projection is provided so as to protrude inside the footwear.

3. A footwear as claimed in claim 2, in which said pressure projection has an angled shape with its middle portion protruding upward in section.

4. A footwear as claimed in claim 1, in which said pressure projection is formed from harder material than that of its surrounding portion.

5. A footwear as claimed in claim 1, in which said pressure projection is provided on the upper surface of a sole.

6. A footwear as claimed in claim 1, in which said pressure projection is provided on a sheet member to be inserted inside the footwear to be under a foot.

7. A footwear as claimed in claim 1, in which said pressure projection is provided inside a band of a sandal.

8. A footsole as claimed in claim 1, in which said pressure projection is provided on the inner surface of an upper of a shoe.

9. A footsole as claimed in claim 1, in which said pressure projection and a sole are integrally molded from synthetic resin.

10. A footwear as claimed in claim 1, in which said pressure projection is fomred separately and then fitted onto a sole.

11. A footwear as claimed in claim 7, in which a sole is provided with said pressure projection and has at least such a flexibility that its portion including said projection is deformable when under a foot.

12. A footwear as claimed in claim 6, in which said pressure projection is provided on at least one portion on the upper surface of a sole selected from the root portion of the root portion of the toes, the arch portion, the portion a little forward from the arch portion a little forward from the arched portion toward the central portion, and the heel portion.

13. A footwear as claimed in claim 1 in which said magnet is disposed so as to be closely adjacent or constant with an effective spot of a footsole.

14. A footwear as claimed in claim 1, in which said magnet is disposed at such a distance from an effective spot of a foot as to permit the application of magnetism to the effective spot.

15. A footwear as claimed in claim 1, in which said magnet is attached onto said pressure projection so as to protrude beyond said projection.

16. A footwear as claimed in claim 1, in which said magnet is embedded in said pressure projection.

* * * * *